United States Patent [19]

Bundy et al.

[11] 4,172,952

[45] Oct. 30, 1979

[54] 11-DEOXY-2,2-DIFLUORO-PGF COMPOUNDS

[75] Inventors: Gordon L. Bundy, Portage; Norman A. Nelson, Galesburg, both of Mich.

[73] Assignee: The Upjohn Company, Kalamazoo, Mich.

[21] Appl. No.: 897,221

[22] Filed: Apr. 17, 1978

Related U.S. Application Data

[62] Division of Ser. No. 609,410, Sep. 2, 1975.

[51] Int. Cl.² ........................................... C07C 177/00
[52] U.S. Cl. .................................................. 560/121
[58] Field of Search ......................... 560/121; 562/503

[56] References Cited

U.S. PATENT DOCUMENTS 3,873,607  3/1975  Bernady et al. ..................... 260/514

*Primary Examiner*—Robert Gerstl
*Attorney, Agent, or Firm*—Robert A. Armitage

[57] ABSTRACT

11-Deoxy prostaglandin type compounds, i.e prostaglandin type compounds in which the 11-hydroxy group is replaced by hydrogen, are disclosed, with processes for making them. These compounds are useful for a variety of pharmacological purposes, including anti-ulcer, inhibition of platelet aggregation, increase of nasal patency, and labor induction at term.

1 Claim, No Drawings

11-DEOXY-2,2-DIFLUORO-PGF COMPOUNDS

The present application is a divisional application of Ser. No. 609,410, filed Sept. 2, 1975, now pending.

The present invention relates to prostaglandin analogs, for which the essential material constituting disclosure therefor is incorporated by reference here from Ser. No. 897,225, filed Apr. 17, 1978, now U.S. Pat. No. 4,126,754, issued Nov. 21, 1978, which is a divisional application of Ser. No. 609,410.

We claim:
1. 11-Deoxy-2,2-difluoro-PGF$_2\alpha$, methyl ester.

* * * * *